United States Patent [19]

Müller et al.

[11] 4,207,200

[45] Jun. 10, 1980

[54] SOLUBLE COMPLEX FORMER FOR THE AFFINITY SPECIFIC SEPARATION OF MACROMOLECULAR SUBSTANCES, ITS PREPARATION AND ITS USE

[76] Inventors: Werner Müller, Rolandstrasse 31; Antonin Eigel, Am Meierteich 15; Hans-Jürgen Schuetz, Geschwister Scholl Str. 1, all of 4800 Bielefeld; Hans Bünemann, Am Pulverbach 8, 4803 Steinhagen, all of Fed. Rep. of Germany

[21] Appl. No.: 888,397

[22] Filed: Mar. 20, 1978

[30] Foreign Application Priority Data

May 8, 1978 [DE] Fed. Rep. of Germany ....... 2712344

[51] Int. Cl.² .................... B01D 15/08; G01N 31/08
[52] U.S. Cl. ................. 252/184; 23/230 R; 252/299; 252/408; 424/2; 422/56
[58] Field of Search ...................... 252/184, 408, 299; 23/253 TP, 230 R; 424/2

[56] References Cited

U.S. PATENT DOCUMENTS

| 2,732,382 | 1/1956 | Minsk et al. | 526/51 |
| 3,544,484 | 12/1970 | Roth | 252/408 |
| 3,904,373 | 9/1975 | Harper | 252/408 |
| 4,070,912 | 1/1978 | McNaughton | 252/408 |

FOREIGN PATENT DOCUMENTS 44-18580 8/1969 Japan ......................... 526/51

*Primary Examiner*—Benjamin R. Padgett
*Assistant Examiner*—Irwin Gluck
*Attorney, Agent, or Firm*—Stevens, Davis, Miller & Mosher

[57] ABSTRACT

The invention provides soluble complex forming agents suitable for specific separation of macromolecular substances and particularly of such biopolymers as nucleic acids. These agents contain soluble polymers, such as polyethyleneglycols of a molecular weight between 200 and 40,000, dextran of a molecular weight of $3 \times 10^{-3}$ to $3 \times 10^{-6}$ and linear polyacrylamides; to these soluble polymers at least one base specific group for nucleic acids is covalently bound. The bonding can be achieved by esterification, grafting, copolymerization or copolycondensation.

17 Claims, 7 Drawing Figures

SOLUBLE COMPLEX FORMER FOR THE AFFINITY SPECIFIC SEPARATION OF MACROMOLECULAR SUBSTANCES, ITS PREPARATION AND ITS USE

The present invention relates to a soluble complex former for the affinity specific separation of macromolecular substances, especially biopolymers, such as mixtures of single strand and/or two strand nucleic acids, especially desoxyribonucleic acids (in the following abbreviated as DNA), a process for the preparation of this complex former as well as its utilization.

The isolation of individual genes or of sets of identical genes in repetitive arrangement from the genome of eucaryotic cells is not only of purely scientific interest but also of great practical importance for gene technology. Such separations were possible only where the base composition of the gene or the gene group with its spacers differed from the mean base composition of the total genome by at least 6 to 7%. For the separation process there were used mostly cesiumion-density gradient centrifugation with DNA-base specific additions such as silver, mercury, or platinum ion or actinomycin, netropsin or the dye Hoechst 33258. These processes have only a limited capacity, are expensive and time consuming.

In recent years, the development of materials for affinity chromatography of polymers has greatly simplified the isolation of a multitude of many biopolymers or made possible their preparation in pure state. In these processes, one usually starts with a carrier material which, after chemical activation, is reacted with a substance which binds the biopolymer to be isolated as specifically as possible. On the basis of this specificity, one can adsorb the desired biopolymer to the chromotographic material, in an ideal case selectively from a mixture of similar substances, and subsequently desorb them under suitable conditions in pure state. (P. Cuatrecasas und C. B. Anfinsen, Ann. Rev. Biochem. 40 (1971) 259 to 278).

In spite of the multitude of examples for the successful utilization of this method for a multitude of biopolymers, no chromatographic material could up to now be developed which enables a similarly selected and programmable separation for mixtures of nucleic acids. A highly resolving fractionation on a gram scale is however a prerequisite for the mentioned isolation of specific genes or sets of identical genes.

In the existing processes for the separation of nucleic acids of lower molecular weight, for instance transfer ribonucleic acid, the separation into the different species is achieved on absorbants which combine ion exchange properties with lipophylic exchange effects (R. M. Kothari und V. Shankar, Journal of Chromotography 98 (1971) 449 to 475). In these processes there are utilized essentially the exchange abilities of the carrier with the rare bases of the nucleic acis which are present in the various transfer ribonucleic acids in varying amounts. Since the high molecular ribonucleic acids and desoxyribonucleic acid usually do not contain rare bases, methods for their separation can only be established according to the following characteristics of distinction:

(a) ratio of single to double strand
(b) difference in base composition
(c) difference in base sequence
(d) difference in molecular weights
(e) difference in tertiary structures All these characteristics are actually used in the fractionation method currently used. (R. M. Kothari, Chromatog. Rev. 12 (1970) 127 to 155).

According to the most effective method, the fractionation in salt gradients in the ultra centrifuge leads to differences according to (b), (c) and (e) in the floating density (schwebedichte) for single DNA species, which can be magnified by the addition of base specific substances. The sharpness of separation decreases with decreasing molecular weight, the capacity decreases with increasing molecular weight. In the adsorption chromatography on hydroxyapatite the fractionation proceeds generally according a and only to a minor extent according to b, whereby guanine-cytosine-rich nucleic acids are already desorbed at somewhat lower salt concentration than the adenin-thyamine-rich components. (W. Pakroppa und W. Müller, Proc. Nat. Acad. Sci. U.S.A., 171 (3) (1974) 699 to 703).

In quite analogous manner, double strand nucleic acids can be fractionated using specific protein silica gel adsorbants (for example, methyl-serum-albumin-silica gel) according to differences in the base composition whereby the guanine-cytosine rich DNA species are again first diluted. (J. D. Mandell and A. D. Hershey, Analytical Biochemistry 1 (1960) 66 to 77; N. Sueoka and Ts'ai-Ying Cheng, J. Mol. Biol. 4 (1962) 161 to 172). The true mechanism of action of these rather accidentally discovered absorbants is not known. For that reason the lower sharpness of separation produced by these materials could not, up to now, be fundamentally improved in spite of all efforts.

Only in the last years, in the coarse of systematic investigation of numerous substances which form complexes with nucleic acids, compounds were discovered which appeared suitable for the desired sysnthesis of materials for affinity chromotography. (W. Müller and D. M. Crothers, Eur. J. Biochem. 54 (1975) 267 to 277; W. Müller, H. Bünemann and N. Dattagupta, Eur. J. Biochem. 54 (1975) 279 to 291 and W. Müller and F. Gautier, Eur. J. Biochem. 54 (1975) 385 to 394). What advantages utilization of such well-investigated substances brought to the separation of nucleic acid mixtures was demonstrable already in the case of the examples of combined use of hydroxy-apatite and ethidium as base specific addition for separation of superhelical DNA and helical DNA (W. Pakroppa, W. Goebel and W. Müller, Analytical Biochemistry 67 (1975) 372 to 383) and of hydroxyapatite in combination with phenyl-neutral red derivatives as base specific complex formers in the separation of double strand DNA-species (W. Pakroppa and W. Müller, Proc. Nat. Acad. Sci. U.S.A., 71 (3) (1974) 699 to 703).

The solution capacity of the last mentioned method is comparable to that of a preparative cesiumchloride density gradient that, means DNA fractions with separation of (G+C)-content of >10% where G represents guanine and C represents cytosine) can thus be separated. In spite of high capacity, this process has a disadvantage, that DNA mixtures of medium molecular weight of components of more than $20 + 10^6$ cannot be managed well and that the special hydroxyapatite used as absorbant must itself be prepared.

It has been known for some time that nucleic acid mixtures in the polyethyleneglcol-dextran-system can be separated under certain circumstances to separate RNA and either single strand DNA or double strand DNA. In this process, the double strand DNA is always enriched in the (lighter) polyethyleneglycol phase, that means it has a higher distribution coefficient than single strand nucleic acids. The absolute values of the distribution coefficients can be varied by addition of potassium or lithium salts to $10^3$ to $10^4$ potency, however a fractionation according to base consistency cannot be achieved with these systems.

The object of the present invention consists in providing a soluble complex former by the use of which the distribution coefficient or the mobility of biopolymers can be selectively varied, according to affinity specificity, so that a base specific separation of biopolymers and especially of mixtures of single strand and/or double strand nucleic acids, especially of DNA mixtures, can be achieved with high capacity.

It has now been found that this task can be solved with a soluble complex former which encompasses a soluble polymer to which at least one residue affinic to the biopolymer is chemically bound.

Thus, it has been found that the distribution of nucleic acids on use of such soluble complex formers can be strongly influenced, if the complex formers have a distribution coefficient strongly varying from 1. This can hardly be found with low molecular compounds in the polyethyleneglycol-dextrane-system but it can be achieved easily according to the invention by binding the low molecular residue, which is affinic to the biopolymer, covalently to suitable polymers, provided that the residue affinic to the biopolymer does not lose its affinity thereby. One achieves distribution coefficients with a value significantly greater than 1 according to this invention by binding to polyethylene glycol (most simply by an esterification reaction) while distribution coefficients with a value considerably lower than 1 can be achieved by binding the biopolymer affinic residue either to dextrane (according to the bromcyan method or by esterification) or incorporation into linear polyacrylamide. If the biopolymer affinic residue is base- or sequence- specific and if this property is maintained after binding to the polymer, guanine-cytosine-rich or adenine thiamine-rich nucleic acids are enriched very effectively in the upper or lower phase of the distribution system.

Subject of the invention is therefore a soluble complex former for the affinity specific separation of macromolecular substances, especially biopolymers, such as nucleic acids, characterized by a soluble polymer, to which at least one residue affinic to that bipolymer is covalently bound.

The complex former of the invention contains as soluble polymer, preferably a polymer soluble in water and/or organic solvents, such as a polyethyleneglycol of a molecular weight of 200 to 40,000, preferably with a molecular weight of about 6,000, a dextran of a $\overline{M}_w$ of $3 \times 10^3$ to $3 \times 10^6$ or a linear polyacrylamide with a degree of polymerization of 200 to 300 (MW 14000 to 21000). In principle, all water soluble polymers containing hydroxy groups are suitable. Preferably, there is bound to the soluble polymer as a residue affinic for the biopolymer a base specific group for nucleic acids. This bonding can be achieved by esterification, by grafting or by copolymerization or by copolycondesation.

As residues affinic to the biopolymers there can be used base specific groups which are described in the quoted literature citations. Especially suitable are the residues of dyestuffs of the following general formulas:

in which general formulas
  X designates a CH-group or a nitrogen atom
  Y designates an oxygen atom, a sulphur atom, an NH-group or a group of the formula:

$R^1$ can each represent hydrogen or methyl independent of what the other group is
  $R^2$ represents a hydrogen atom or a methyl group
  $R^3$ a hydrogen atom or a methyl group
  $R^4$ a hydrogen atom or a methyl group, and
  $A^\ominus$ an anion, such as a chloride anion, a perchlorate anion, or an oxylate anion.

Especially preferred for the base specific complex builders bound to the polymeric carrying material are the residues of the following dyestuffs:

| 1.Diamidino-phenyl-indole (DAPI) |  |

-continued

2. Malachite green

3. Crystal violet

4. Methyl green

5. Auramine

6. Dyestuff Hoechst 33258

7. Di-tert.-butyl-proflavin

8. Di-tert.-butyl-acriflavin

9.

-continued

10.

11.

12.

R = H, Alkyl, Aminoalkyl

13.

14.

15.

16.

17.

18.

-continued

19.

20. Proflavin

21.

22.

23.

24.

25. Thionine

26. Acridin Orange

27. Pyronin G

28. Thiopyronin

29.

30.

31. Methylene blue

In the above formulas Me represents the methyl group.

The base specific groups most preferred according to the invention, however, are the residues of phenyl neutral red of the formula:

and malachite green of the formula:

These dyestuffs are known and available in commerce or can be prepared according to methods known to the expert and described, for example in the above publications of W. Müller and D. M. Crothers. (Eur. J. Biochem. 54 (1975) 267 to 277), W. Müller, H. Bünemann and N. Dattagupta (Eur. J. Biochem. 54 (1975) 279 to 291) and W. Müller and F. Gautier (Eur. J. Biochem. 54 (1975) 385 to 394).

These base specific groups or dyestuff residues can be bound by methods which are quite familiar to the experts covalently to the soluble polymers, for example by esterification with hydroxyl groups on the polymers (polyethylene glycol or dextrane) through use of carboxyl groups introduced into the dyestuff molecule, by amide formation, by urethane formation or also by copolymerization in absence and preferable in presence of other copolymerizable monomers by use of copolymerizable double bonds, which are introduced into the dyestuff molecule, for example an acrylamide group as is the case in the base specific dyestuffs acrylphenyl neutral red and acrylmalachite green of the following formula, which are preferred for the purposes of this invention:

-continued

These base specific dyestuff derivatives can be prepared by methods known to the those skilled in the art by introduction of the acryl residue into the named dyestuff molecules. This is applicable also for the previously mentioned dyestuff molecules.

According to this invention, one uses as soluble polymer, preferably an unwetted and in water and organic solvents soluble or quellbar (swellable) polymer, such as a polyethyleneglycol of a molecular weight of 200 to 40,000, preferably of a molecular weight of 6,000, a dextrane of a $\overline{M}_w$ of $3 \times 10^3$ to $3 \times 10^6$, or a linear polyacrylamide of a degree of polymerizatin of 200 to 300. These polymers show no major exchange effects with biopolymer affinic residues and especially for nucleic acid base specific groups.

The subject matter of the invention is also a process for the preparation of the above-defined soluble complex formers which is characterized by the fact that one binds the residue affinic to the biopolymer to the soluble polymer by use of a group which reacts with a functional group of the soluble polymer.

Thus, one can combine the biopolymer affinic residue by esterification, amide formation, urethane formation, grafting (aufpfropfen) or by copolymerization or copolycondensation with the starting materials necessary for the construction of the soluble polymer to the soluble polymer, for which purpose one uses usual reagents and usual reaction conditions and one introduces the groups suitable for these reactions into the soluble polymer or introduces the residue affinic for that biopolymer.

Thus, one can bind a carboxyl group carrying residue affinic to the biopolymer by esterificaton with hydroxyl group on polyethelene glycol or dextrane or one can build in a biopolymer affinic residue containing a copolymerizable double bond into linear polyacrylamide by copolymerization. It is also possible to bind the biopolymer affinic residue according to the bromocyan method.

However, it is preferable to conduct the esterifcation of a biopolymer affinic residue containing a free carboxyl group using polyethyleneglycol by use of a melting reaction in which an aliphatic or aromatic tertiary amine, especially imidazol is used as a catalyst, working in presence of a suitable condensation agent, for example in the presence of an aromatic sulfonylchloride such as toluolsulfonylchloride, diisopropylsulfonylchloride or Di-tert-butylsulfonylchloride. Further examples for the introduction of groups affinic to the biopolymer by esterification are the esterification of polyethyleneglycol 6000 with p-nitrobenzylic acid of 4'-carboxymalachite green (Chrome green).

For the purpose of incorporation of biopolymer affinic residues into linear polyacrylamide one starts with the corresponding amino derivatives of the named dyestuffs. Which, after transformation into the acrylamino derivatives, using acylamide, can be copolymerized to linear copolymers. The incorporation of a beta-alanyl residue between the amino function and the acryl groups, while useful for the DNA exchange effect, is however, not absolutely necessary.

With the aid of the soluble complex formers of the invention, biopolymers such as proteins, and especially DNA-mixture, can be complexed specifically, since the residue affinic to biopolymers accumulates specifically at the biopolymers regarding the bases (A, C, G or T respectively). Thereby a specific change of properties of the complex biopolymers in solution can be achieved. Thus, there can be achieved by the complexing of biopolymers with soluble complex formers of this invention a strong modification of the distribution coefficient of the complexed biopolymers which can be utilized for separation.

Furthermore, complexing of the biopolymers with the aid of complex formers according to this invention, can be used to influence the hydrodynamic friction resistance of the molecules which produces great changes in mobility which can be utilized in gelelectrophoresis for separation of the biopolymers.

The capacity to dissolve nucleic acids which can be achieved by use of the soluble complex formers of this invention, and especially on the basis of polyethyleneglycol in the two-phased distribution or the gelelectrophoresis, is far greater than could be achieved with other methods up to now. Thus, it becomes possible to achieve the abovementioned isolation and pure preparation of biopolymers in a simple and effective manner.

Subject of the invention is thus also the utilization to the above refined soluble complex formers for separation of biopolymers, especially nucleic acids by two-phase affinity distribution, by two-phase -separation chromatography or by gelelectrophoresis, wherein the complex formers of the invention serve as means for influencing the distribution coefficient or mobility of the biopolymer.

If one wants to conduct the two-phase distribution chromatography with the aid of a continuously working chromatographic column process, it is preferred to use cellulose as carrier which binds for example the heavier, dextrane-rich phase of the separation system adsorptively or physically, respectively. In this manner, one can, using cellulose, change all separation processes on the basis of aqueous polymer-polymer or polymer-salt systems, respectively (see also, P. A. Albertson (1971) "Partition of Cells, Particles and Macromolecules" 2nd edition, Almquist and Wicksell, Stockholm), especially from polyglycoldextrane systems in columa-chromatographic multi-step separation systems.

The soluble complex formers of this invention are especially suitable for the separation of mixtures of single strand and/or double strand nucleic acids, particularly of DNA mixtures.

In the two-phase affinity separation, the two-phase chromotography and the gelelectrophoresis one uses usual basic media, for example phosphate buffer or tris-buffer with a concentration of about 10 mMol/l, pH and a pH-value in the range of 4.5 to 8; in the case of the complex formers of the invention which contain as the base specific group the residue of malachite green, a weakly acid buffer of a pH value of 5.5 to 6 is used, for example an 0.01 molar phosphate of a pH value of 5.5 to 6. As eluting agent one uses the mobile phase, that is the polyethyleneglycol-rich phase which can contain salts as additives, preferably akali metal salts, such as sodium chloride, sodium perchlorate, lithium perchlorate, potassium chloride, lithium sulfate, potassium acetate, etc. It is advantageous to use concentration gradients with decreasing or increasing ($LiSO_4$) concentration.

The salt gradients optimal for separation, their constituents, concentrations, pH-values and the buffers used for that purpose can be ascertained by one skilled in the art without difficulty. In the following the present invention is further described by examples and by reference to the attached drawings. In the drawings are shown:

EXAMPLE 1

Preparation of polyethyleneglycol-1-methyl-4'-carboxyphenyl-neutral red half esters (A) 1-methyl-4'-carboxyphenyl-neutral red (1,2-dimethyl-3-amino-5-(4'-carboxyphenyl)-7-dimethylaminophenazinium salt)

One dissolves 1.05 g N-dimethylaminoaniline dihydrochloride in 50 ml of methanol and treats the solution in the stated sequence with 2 ml 2n-hydrochloric acid, 0.62 ml. 2,3-dimethylanilin, 5 ml acetate buffer (1 m sodium acetate and 1 m acetic acid) and 20 ml 1/6m-potassium iodate solution. After 7 to 8 minutes, one dilutes the deep green solution with methanol to 220 ml and adds 13.7 g p-aminobenzoic acid. After solution of the acid, one dilutes with water to 320 ml, lowers the pH value using 2 n-sodiumcarbonate solution to 6.7 and heats on a heating plate in the course of 30 minutes under stirring to 50° C. At that temperature, one adds a further portion of 10 ml 1/6 n-potassium iodate solution and heats slowly under stirring to boiling. At a temperature of about 70° C. the reaction mixture turns from blue violet to red. The mixture is concentrated to 165 ml (boiling temperature=78° C.) and thereafter stored at 3° to 4° C. for 12 hours. The separated material is vacuum filtered, washed with cold water and dried over potassium hydroxide in vacuum.

The dry crude product is extracted after polymerization in a Soxhlet extraction apparatus with about 350 ml acetone for 6 hours in order to remove the unreacted p-aminobenzoic acid, after which one dissolves the crude dyestuff with 350 ml methanol in the same apparatus from the shell. After evaporation of the methanol under vacuum, one purifies the residue chromotographically on polyamide (for example, SC6>0.07 of the firm Macherey and Nagel) in chloroform/benzene/methanol/water-system (60/25/15/0.4 volume/volume). The eluate of the principal zone is evaporated to dryness at a bath temperature of 35° C. under vacuum after which the residue is recrystallized from pure ethanol or n-propanol. The yield is about 700 mg (which corresponds to 36% of theory).

(B) Esterification of 1-methyl-4'-carboxyphenyl neutral red with polyethyleneglycol (6000 or 10,000).

One melts 3 g at 80° C. under stirring with 3 g imidazole and then treats with 50 mg of 1-methyl-4'-carboxyphenyl neutral red obtained according to Step A. When all of the dye has dissolved, one adds 600 mg p-toluenesulfonyl chloride and heats the melted mass for an additional 8 to 12 hours under the exclusion of moisture at 90° C. After that time, more than 90% of the dyestuff has reacted.

One dissolves the molten mass while cool in about 50 ml of a 0.01 n-sodium phosphate buffer of a pH value of 5.6. After 3° hours, one filters at 4° C. and chormatographs in the same medium over chemically wetted dextran (sephadex G25) for removal of unreacted dyestuff, imidazole and toluenesulfonyl acid. The eluate of the principal zone is stored in darkness at 3° to 4° C.

If the unreacted polyethylene glycol is also to be removed (which is not necessary for most purposes in use), one extracts the solution with chloroform, evaporates the chloroform under vacuum, dissolves the residue in water and adsorbs the ester on wetted dextran (sephadec G60 CM). After washing out the polyethylene glycol with water the ester is desorbed using 1-m-potassium chloride solution, whereupon one dialyzes the eluate against a buffer of a pH value of less than 7. In order to determine the content of the solution, one determines the optical density of the solution at 555 nm in presence of 2% sodium dodecyl sulphate. The molar extension coefficient of the ester in this medium is 53,000 (Mol$^{-1}\times$cm$^{-1}$).

EXAMPLE 2

Two-phase affinity distribution of mixtures of double helical desoxyribonucleic acids.

Figure 1:
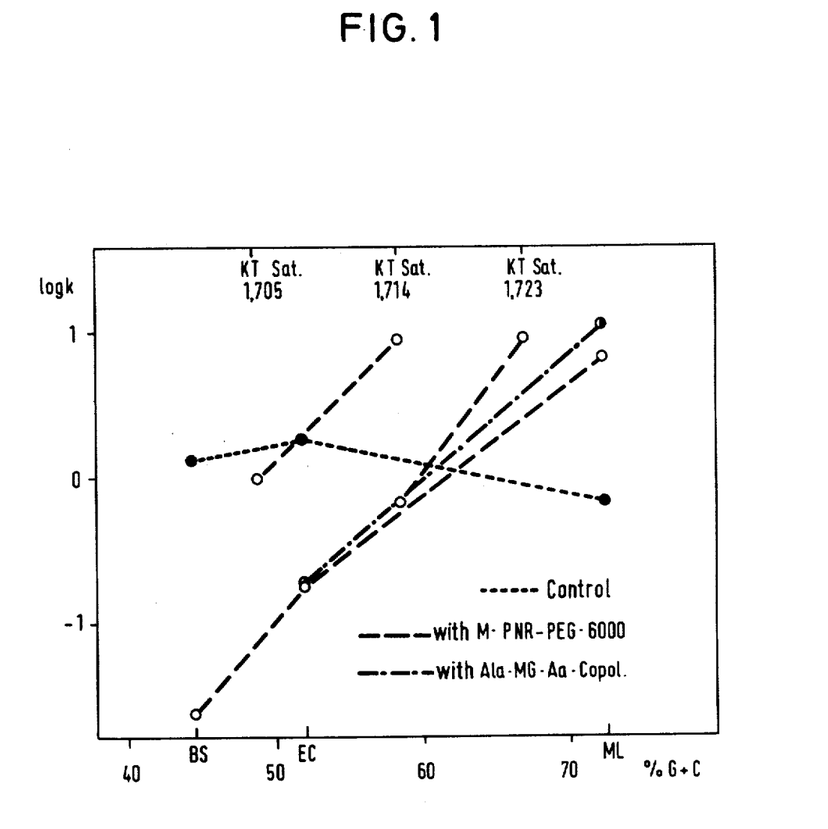
FIG. 1: On the basis of curves, the change in distribution coefficient K with the DNA-base composition in polyethyleneglycol-dextrane-system in the presence of GC-specific polyethyleneglycol bound 1-methylphenyl neutral red (KTSat=caef sthymus-DNA satellites)

If one adds to a system of polyethyleneglycol-6000 and dextrane-T500 with adjusted potassium chloride and lithium sulphate content, so much polyethylene glycol bound 1-methylphenyl neutral red (M. BNR-PEG.6000) that the upper phase contains $4\times10^{-5}$ mol of the dye per liter it is possible by using the distribution coefficients given in FIG. 1 to separate in this mixture desoxyribonucleic acids of different base conposition or to cause a great enrichment. One achieves this same result if one adds to the system in place of the CG-specific phenyl neutral red derivatives so much AT-specific alanylacrylamino malachite green acrylamid copolymer (Ala.MG.Aa.Copol.) that the concentration of the dyestuff in the lower phase of the system amounts to about $3\times10^{-5}$ mol per liter.

In both cases, it is possible to enrich the upper or the lower phase respectively by one separation step with desoxyribonucleic acid of $\Delta(G+C)$ values of 15 to 20% of greater than 90% purity. If the difference between the (G+C)-content is only 8% it is possible to obtain a component in 80% yield in a purity of more than 9% in the upper phase and a second component in a purity of 75 to 80% from the lower phase.

The combined use of GC and AT-specific complex formers gives stir better results.

Figure 2:
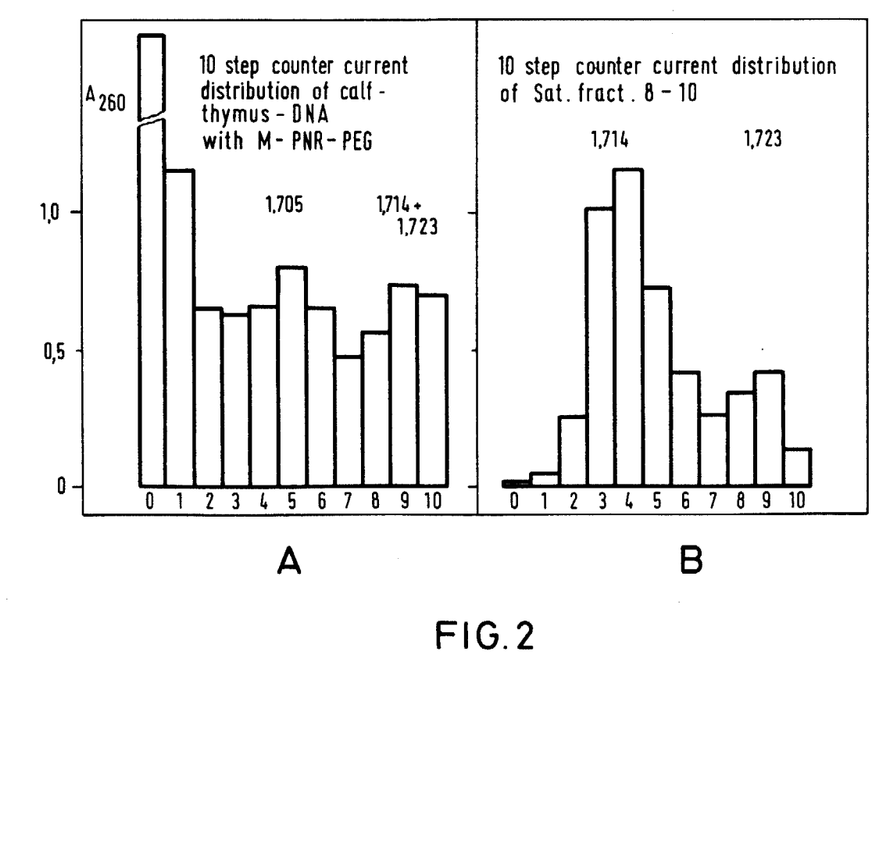
FIG. 2A: The ten-step counter current distribution of calf-thymus-DNA for separation of the GC-rich satellite fraction in polyethyleneglycol-dextrane-system with polyethyleneglycol-1-methylphenyl neutral red.
FIG. 2B: The ten-step counter current distribution of satellite fraction 8–10 of FIG. 2A for separation into the components of floating density 1,714 and 1,723 (Cesium chloride density gradient) in polyethyleneglycol-dextrane-system in the presence of polyethyleneglycol bound 1-methylphenyl-neutral red.

By use of the described distribution system, with GC-specific polyethyleneglycol bound 1-methylphenyl neutral red in 10 step counter current distribution it is possible to separate the GC-rich satellites from calf-thymus-DNA (FIG. 2A) and to separate them into their main components under changed conditions (FIG. 2B).

EXAMPLE 3

Two phase distribution chromatography of DNA mixtures

The multi-step distribution of mixtures of substances can always be developed into a chromatographic separation process if it is possible to find a carrier for both phases which attahces the phase sufficiently strongly.

Up to now, only silica gel and sephadex gels have been proposed as carriers for the polyethyleneglycol-dextran system. In review of these data, it has been found that silica gel does not bind the dextran system sufficiently to make it suitable for larger separation columns. Sephadex gels, as well as agarose, are unsuitable because of their undesirable molecular sieve effect.

Very useful has proven cellulose powder, especially defatted, acid washed linter (for example the material obtained from the firm Machery and Nagel 2200 ff). After adequate preswelling one g of this cellulose binds about 1 to 1.2 ml of the lower phase of a system of polyethylene glycol 6000 and dextran-T40 (of a mean molecular weight of 42,000).

If one prepares a two-phase distribution column, using 10 g of cellulose preswelled at a temperature of more than 26° C. (which is sufficient for separation of 1.5 mg of a DNA mixture) in the usual manner, it is possible then to carry out the separations according to FIGS. 3 and 4.

Figure 3:
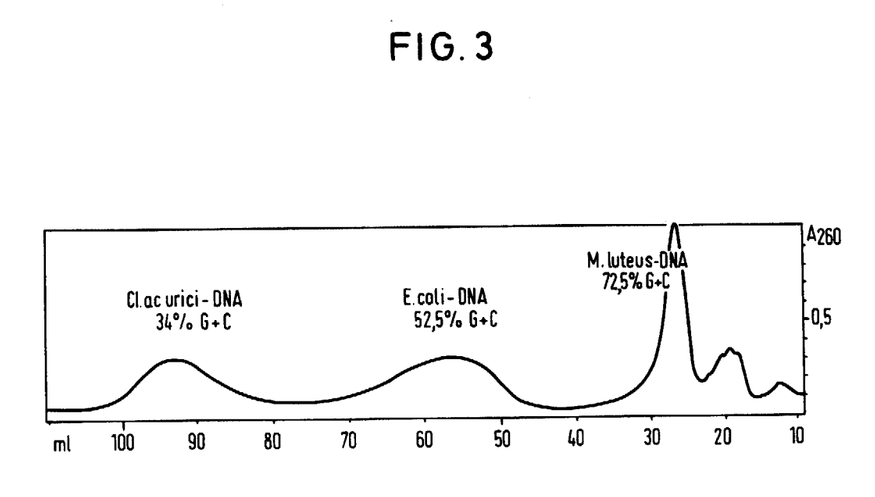
FIG. 3: The two-phase chromatography of 3 bacterial DNA of different GC-content in polyethyleneglycol-dextran system under addition of polyethyleneglycol bound 1-methylphenyl neutral red on cellulose.

FIG. 3 shows the two-phase chromotography of three bacterial desoxyribonucleic acids of different G+C-content in a system polyethyleneglycol-dextrane under addition of polyethylene bound 1-methyl-phenyl neutral red on celluloce. The zones are 12 to 20 ml eluate volume originate from disturbances of the excess dyestuff and excess lower phase respectively).

Figure 4:
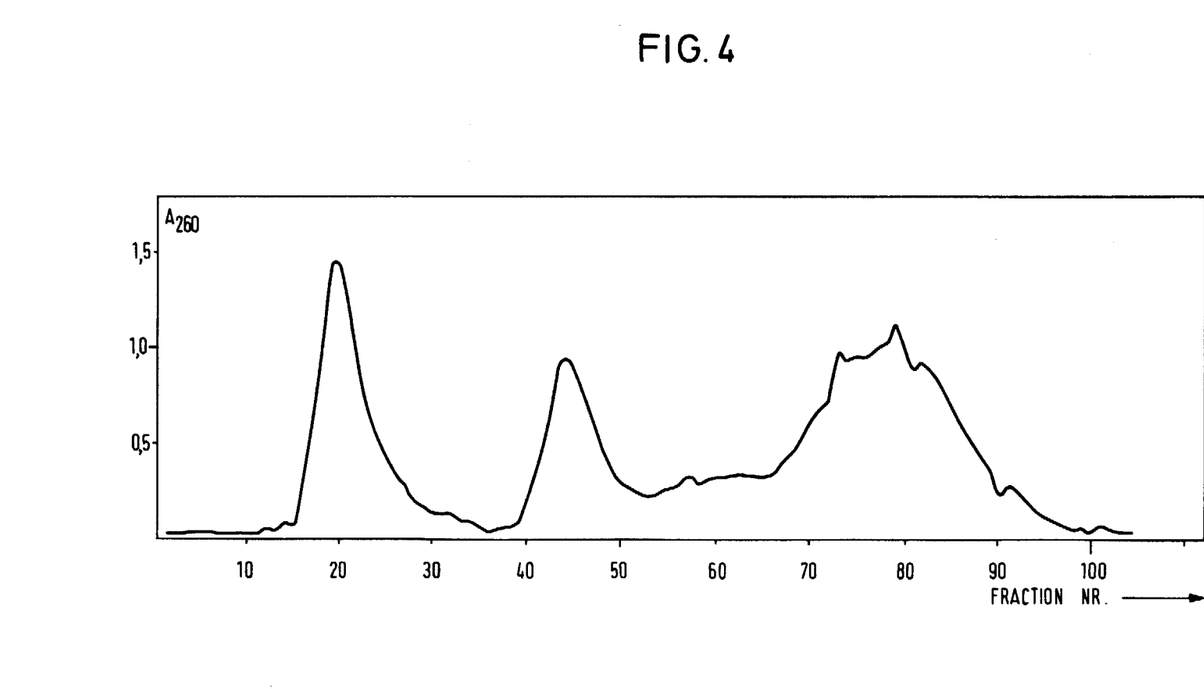
FIG. 4: shows the two-phase chromotography of calf-thymus-DNA in polyethyleneglycol-dextrane-system with polyethyleneglycol bound 1-methylphenyl-neutral red on cellulose.

FIG. 4 shows two-phase chromatographic of calf-thymus-DNA in polyethyeneglycol-dextran system, with polyethylene bound 1-methyl-phenyl-neutral red (2.2 OD555/ml upper phase) on cellulose. The peak of the fraction number 20 contains the GC rich satellites while the peak between the fractions 40 and 50 contains a GC-poor DNA fraction of a floating density of 1.705 in cesium chloride density gradient. The peak between fractions 67 and 93 contains the so-called "main-band"-DNA. If the components of the DNA mixture differ by more than 6% in GC content, one uses in the above two-phased distribution in the upper phase, a K$^+$—Li$^+$-gradient in order to obtain a sufficiently great migration velocity of the GC- or AT-poorest components respectively.

The work of temperatures of more than 26° C. (the sums in FIGS. 3 and 4 were all carried out at 30° C.) did not prove necessary since hereby is assured a sufficiently high of fusion rate of the DNA and a sufficiently low vicosity of the phases.

EXAMPLE 4

Utilization of the inventive polymer bound base specific complex formers in gelectrophoresis of nucleic acid Nucleic acids can be separated by gelectrophoresis, in polyacrylamide or agarose gels according to their molecular size. The combined utilization of both gels permits under certain conditions also a moderate separation according to base composition. For a separation preferably according to base composition there are unsuitable lower molecular base specific complex formers, since the effect of partial charge neutralization on mobility of the electrolytes in the field of tension is relatively small. However, if one adds to the gel a base specific complex former according to the invention, there results a strong mobility change in the GC-and AT-rich desoxyribonucleic acids respectively, that is in dependence of the specificity of the complex former.

This effect can be explained on the basis of the strong changes in hydrodynamic properties which a linear polymer experiences due to the branching caused by the base specificity complex former.

Figure 5:
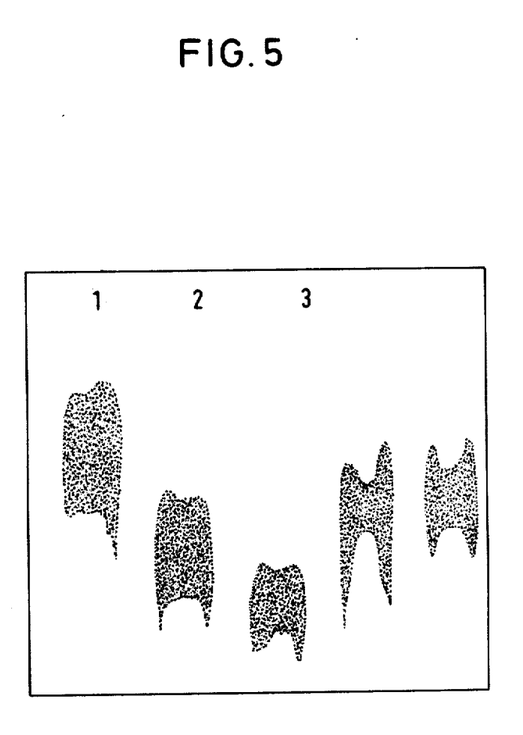
FIG. 5: shows the result of gelelectrophoresis of 3 bacterial desoxyribonucleic acid in the presence of polyethyleneglycol bound 1-methylphenyl-neutral red.

In FIG. 5, are illustrated the changes in mobility for 3 bacterial desoxyribonucleic acids which are "sheared" to the same median size ($\overline{M}_w$=750,000) in agarose in the presence of polyethylene glycol bound 1-methylphenyl neutral red (1.5 OD$_{555}$/ml). In the case of the bacterial desoxyribonucleic acids the following three materials were used:

1: DNA from Cl. acidi urici, 34% G+C
2: DNA from E. coli, 52.5% G+C;
3: DNA from M. luteus, 72.5% G+C.

The FIG. 5, shows a UV-fluorescence photography after dying of the desoxyribonucelic acid with eth dium bromide.

If the nucleic acid mixture to be analyzed consists of components of varying size, one conducts usefully a preliminary separation in round gel without complex former, then beds the round gel into a flat gel with complex former and conducts an electrophoresis vertically to the first direction of separation. If all components have the same base composition, they migrate along to a straight line, which forms an angle of 0° to 90° against a direction of the bedded round gel (see FIG. 6).

Components which do not migrate along this line, show a base composition varying from the mean. If the complex former is GC-specific, more rapid components are richer in AT and slower components are richer in GC than the mean value.

Figure 6:
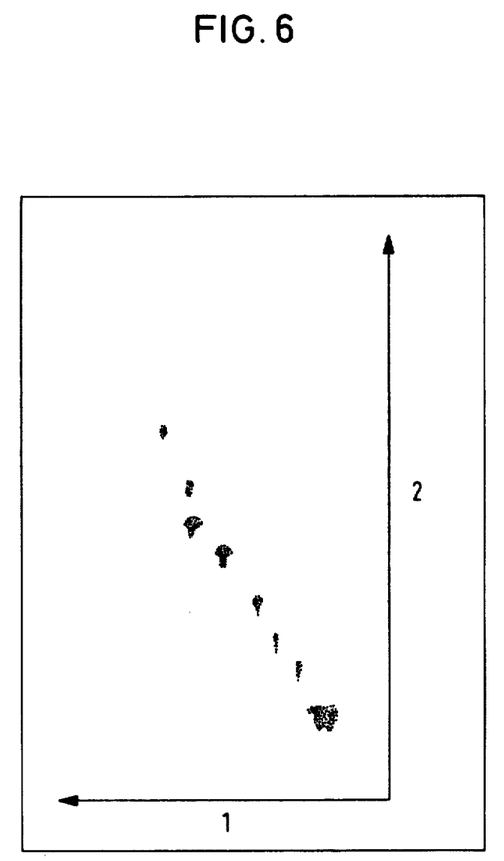
FIG. 6: shows the result of two dimensional agarose gelelectrophoresis in presence of polyethyleneglycol bound 1-methylphenyl-neutral red.

FIG. 6 shows, on the basis of UV-fluorescence photography after dying of the desoxyribonucleic acid with ethidium bromide, the separation of an eco-RI hydrolysate of λ-phage.-DNA with an GC-specific complex former. Therein, fragments were first separated according to size in round gel in direction 1 and then they were subjected to a new electrophoresis in direction 2 in flat gel in presence of the adsorbant according to the invention. Besides the appearance of a normally not visible component, several fragments show clear deviation from the straight line.

In summary, it is to be noted that the complex formers of the invention are excellantly suitable for the separation of macromolecular substances, in particular the biopolymers such as nucleic acid mixtures. These complex formers can be prepared in a simple manner and targeted according to their base specificity.

We claim:

1. Soluble complex former for the affinity-specific separation of macromolecular substances, especially biopolymers, such as nucleic acids, containing a soluble polyethyleneglycol having a molecular weight between 200 and 40,000, a soluble dextran or a soluble linear polyacrylamide, to which at least one base specific group for nucleic acid is covalently bound.

2. Complex former according to claim 1, characterized by the fact that it contains a polyethyleneglycol of a molecular weight of about 6000.

3. Soluble complex former according to claim one wherein the base specific group is bound by esterification, by grafting or by copolymerization or copolycondensation.

4. Complex former according to claim 2 characterized by the fact that it carries as base-specific group for nucleic acids the residue of a dyestuff of the following general formulas I or II:

in which general formulas
X represents a CH-group or a nitrogen atom
Y represents an oxygen atom, a sulphur atom, or an NH-group or a group of the formula:

R$^1$ can represent a hydrogen atom or methyl group and can be different or identical
R$^2$ a represents a hydrogen atom or a methyl group
R$^3$ a hydrogen atom or a methyl group
R$^4$ a hydrogen atom or methyl group, and
A$^\ominus$ an anion such as a chloride anion, a perchlorate anion or an oxylate anion.

5. A complex former according to claim 4, characterized by the fact that it carries as base-specific group the residue of malachite green, crystal violet, methyl green, auramine, the dyestuff Hoechst 33258 of di-tert.-butyl-proflavin, of di-tert.-butyl-acriflavin, of Diamidino-phenyl-indol (DAPI) of 1-methylphenyl-neutral red or of ethidium bromide.

6. Complex former according to claim 4 characterized by the fact that the base-specific group corresponds to the formula:

7. Complex former according to claim 4, characterized by the fact that the base-specific group corresponds to the following formula:

8. Process for the preparation of soluble complex formers according to claim 1, containing a soluble polymer of the class consisting of polyethyleneglycol having a molecular weight between 200 and 40,000, a soluble dextran or a soluble linear polyacrylamide, to which at least one base specific group for nucleic acids is covalently bound, characterized by the fact that the base specific group for nucleic acids is bound to the soluble polymer by a group which reacts with a functional group of the soluble polymer.

9. Process according to claim 8, characterized by the fact that one binds to the soluble polymer the base specific group by esterification, amide formation, urethane formation, by grafting or by copolymerization or copolycondensation with the starting materials required for the preparation of the soluble polymers.

10. Process according to claim 8, characterized by the fact that one binds the base specific group carrying a carboxyl group by esterification with the hydroxyl group of polyethyleneglycol or dextran.

11. Process according to claim 9, wherein one incorporates a radical in the base specific group which contains a copolymerizable double bond by copolymerization into a linear polyacrylamide.

12. Process according to claim 8, wherein one attaches the base specific group to dextran by the cyanogen bromide method.

13. Process according to claim 10, wherein one esterifies polyethyleneglycol in a melting reaction, using imidazole as a catalyst, in the presence of a suitable condensation agent with a base specific group which carries a free carboxyl group.

14. Process according to claim 13, characterized by the fact that one uses as condensation agent toluenesulfonyl chloride.

15. Use of complex formers according to claim 1 for separation of biopolymers, especially nuleic acids, by biphasic affinity distribution, by biphasic partition chromotography, or by genelectrophoresis as means for affecting the distribution coefficient or the mobility of the biopolymer.

16. Use according to claim 15, characterized by the fact that one conducts the biphase distribution chromotography in presence of cellulose as carrier.

17. Use according to claims 15 or 16 for the separation of mixtures of single strand and/or two strand nucleic acids, especially of DNA-mixtures.

* * * * *